United States Patent [19]

Kurokawa et al.

[11] Patent Number: 6,010,666
[45] Date of Patent: Jan. 4, 2000

[54] DEODORIZING METHOD, DEODORIZER, METHOD OF MANUFACTURING DEODORIZER, AND DEODORIZING APPARATUS

[75] Inventors: Tetsuya Kurokawa; Chihiro Kobayashi; Tomonori Tokumoto; Masahiro Yamamoto; Takashi Tsuchida, all of Fukuoka, Japan

[73] Assignee: Toto, Ltd., Fukuoka, Japan

[21] Appl. No.: 08/737,648

[22] PCT Filed: Mar. 22, 1996

[86] PCT No.: PCT/JP96/00748

§ 371 Date: Nov. 15, 1996

§ 102(e) Date: Nov. 15, 1996

[87] PCT Pub. No.: WO96/29099

PCT Pub. Date: Sep. 26, 1996

[30] Foreign Application Priority Data

Mar. 23, 1995 [JP] Japan .................................. 7-091485

[51] Int. Cl.[7] .............................. A61L 9/00; B01J 20/30; B01J 23/34; A62B 7/00
[52] U.S. Cl. ............................. 422/122; 422/5; 502/34; 502/150; 502/300; 502/324; 502/416; 502/417; 502/345; 502/344
[58] Field of Search .......................... 422/5, 122; 502/34, 502/150, 300, 324, 344, 345, 416, 417

[56] References Cited

U.S. PATENT DOCUMENTS

| | | | |
|---|---|---|---|
| 3,773,044 | 11/1973 | Wallace | 128/202.22 |
| 4,572,178 | 2/1986 | Takase et al. | 128/205.27 |
| 5,292,479 | 3/1994 | Haraga et al. | 422/5 |
| 5,568,230 | 10/1996 | Reddy et al. | 399/100 |

FOREIGN PATENT DOCUMENTS

| | | |
|---|---|---|
| 60179125 | 9/1985 | European Pat. Off. . |
| 44-22173 | 9/1969 | Japan . |
| 49-98763 | 9/1974 | Japan . |
| 1304232 | 7/1989 | Japan . |
| 4156854 | 5/1992 | Japan . |
| 5317392 | 3/1993 | Japan . |
| 7016465 | 1/1995 | Japan . |

*Primary Examiner*—Mary E. Mosher
*Attorney, Agent, or Firm*—Carrier, Blackman & Associates, P.C.; Joseph P. Carrier; William D. Blackman

[57] ABSTRACT

Hydrogen sulfide is dehydrogenated to generate a HS group and an S group. The HS group is oxidized to generate sulfuric acid, which is bonded to a metal. The S group is polymerized with a $CH_3S$ group to generate methyl trisulfide or methyl tetrasulfide, which is adsorbed to an adsorbent. Methyl mercaptan is dehydrogenated, for example, to generate a $CH_3S$ group. A portion of the $CH_3S$ group is oxidized to generate methanesulfonic acid, which is bonded to a metal. Another portion of the $CH_3S$ group is polymerized with the $CH_3S$ group itself to generate methyl disulfide, at least a portion of which is adsorbed to an adsorbent. Still another portion of the $CH_3S$ group is polymerized with the S group to generate methyl trisulfide or methyl tetrasulfide, which is physically adsorbed to an adsorbent. In this manner, malodor components including hydrogen sulfide and methyl mercaptan can efficiently be removed without producing or release of harmful secondary products. A simple-structure, compact deodorizing apparatus including appropriate metal oxide catalyst and an adsorbent material suitable for achieving the above deodorizing functions is incorporated in a toilet bowl.

18 Claims, 16 Drawing Sheets

WASHED WITH WATER TWICE
PEAK OF $KMn_8O_{16}$ IS PRESENT

POWDER DIFFRACTION PATTERN (cps)

WASHED WITH WATER THREE TIMES

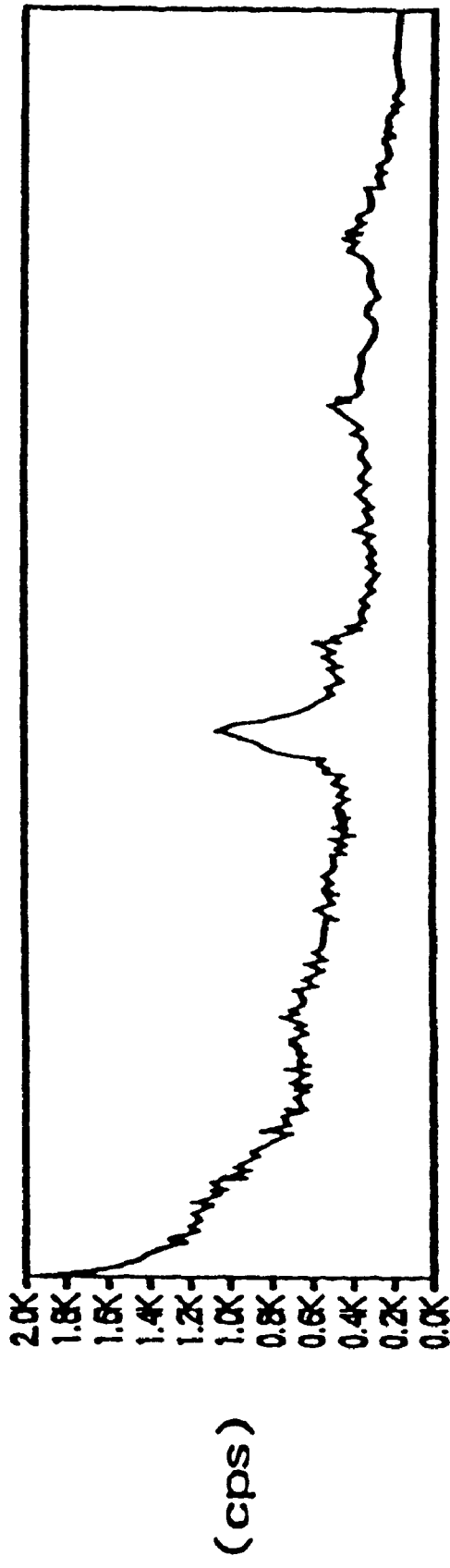

EFFECT OF WATER WASHING ON SPECIFIC SURFACE AREA OF $MnO_2$

XRD PATTERN OF CATALYST OF $MnO_2$ - CuO

| | $H_2S$ | $CH_3SH$ | METHYL DISULFIDE |
|---|---|---|---|
| 5 | 97.8 | 95 | 0 |
| 30 | 92.4 | 90 | 0 |
| 60 | 94.2 | 90.5 | 0.26 |
| 90 | 93.1 | 90.6 | 0.36 |
| 120 | 92.2 | 88.3 | 0.45 |
| 150 | 91.1 | 88.2 | 0.55 |
| 180 | 91.2 | 86.6 | 0.54 |
| 210 | 89.8 | 86.9 | 0.61 |

DEODORIZING PERFORMANCE OF DEODORIZING DISK FAN

FAN DIMENSIONS φ98mm×ʰ13mm
AIR FLOW RATE 70 LITERS/MIN
INLET GAS : $H_2S$=5ppm, $CH_3SH$=5ppm
20°C, 60%RH, Wet Air Balance

FIG. 14(a)
BEFORE TOILET WAS USED
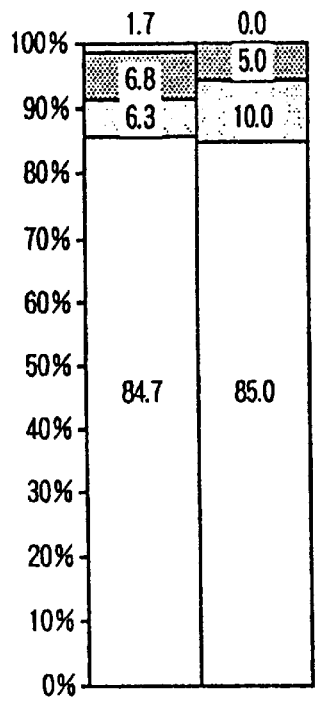
FIG. 14(b)
WHILE TOILET WAS USED
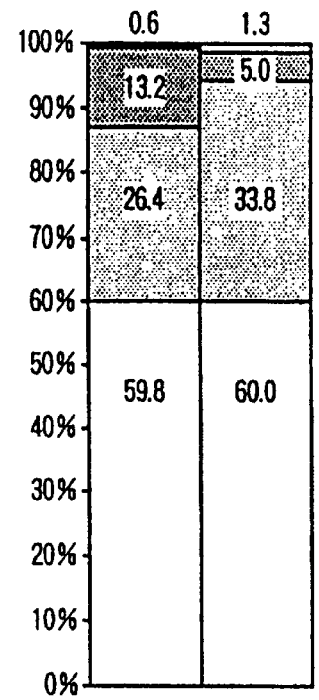
FIG. 14(c)
AFTER TOILET WAS USED
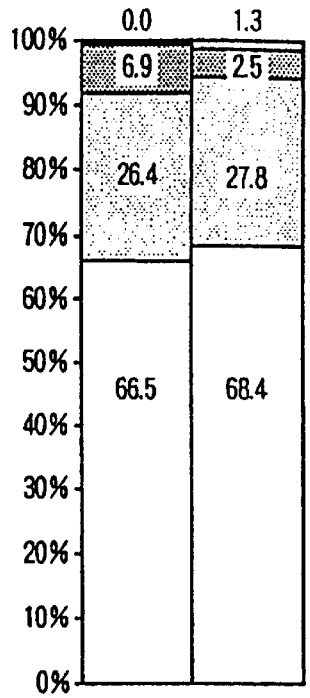
COMPARATIVE RESULTS OF QUESTIONNAIRES ON TOILET SEAT WITH BUILT-IN DEODORIZING FAN AND TOILET SEAT WITH BUILT-IN OZONE DEODORIZING UNIT
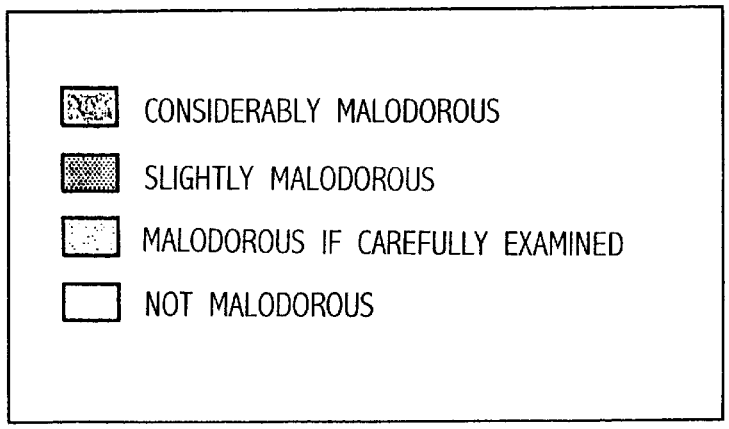

DEODORIZING METHOD, DEODORIZER, METHOD OF MANUFACTURING DEODORIZER, AND DEODORIZING APPARATUS

BACKGROUND OF THE INVENTION

1. Technical Field

The present invention relates to a deodorizing method based on a polymerization reaction, an oxidization reaction, and adsorption, a deodorizer composed primarily of a metal oxide which performs a catalytic action, a method of manufacturing such a deodorizer, and a deodorizing apparatus which incorporates such a deodorizer.

2. Background Art

Conventional deodorizing methods include a masking process, an adsorption process, an ozone deodorizing process, and a catalytic process which uses a metal oxide.

The masking process vaporizes and disperses an aromatic liquid or solid for people to lose a sense of odors. The adsorption process employs an adsorbent such as activated carbon or the like to adsorb odor components. The ozone deodorizing process serves to decompose odor components with ozone. According to the catalytic process, odor components are oxidized and modified by the oxidizing capability of a metal oxide which is used.

In the masking process, since the aromatic material is eliminated in a short period of time, it has to be replaced periodically and frequently. The adsorption process needs periodic replacement of the adsorbent because the adsorption capacity thereof is limited.

The ozone deodorizing process is capable of producing a deodorizing effect for a long period of time. However, the ozone deodorizing process is expensive to carry out as it requires an apparatus for generating ozone and a catalyst for decomposing excessive ozone. The catalyst needs to be regenerated by heating or the like. Furthermore, if ozone is generated at a concentration higher than a designed level thereby deactivating the catalyst, then the ozone harmful to human beings is likely to leak out of the deodorizing apparatus. When a sulfur-based odor is to be deodorized by the ozone deodorizing process, a trace amount of toxic gas of $SO_3$ is discharged.

The catalytic process which uses a metal oxide can maintain a deodorizing effect for a long period of time and does not produce hazardous substances. However, the catalytic process may produce other odor components. Specifically, when hydrogen sulfide ($H_2S$) and methyl mercaptan ($CH_3SH$), which are major components of a fecal odor, are brought into contact with a metal oxide such as $MnO_2$ or CuO, the methyl mercaptan is dehydrogenated and dimerized into methyl disulfide ($CH_3$—S—S—$CH_3$) which has a lower odor intensity. However, if methyl disulfide is brought into contact with a metal oxide when both hydrogen sulfide and methyl mercaptan are present, then a polymerization reaction occurs which generates methyl trisulfide ($CH_3$—S—S—S—$CH_3$) and methyl tetrasulfide ($CH_3$—S—S—S—S—$CH_3$). These generated substances are as malodorous as methyl mercaptan, and cannot effectively be deodorized.

SUMMARY OF THE INVENTION

To solve the above problems, a deodorizing method according to the present invention, carries out a polymerization reaction for polymerizing malodor components with each other, an oxidization reaction for oxidizing malodor components, and an adsorption reaction for adsorbing malodor components to an adsorbent, simultaneously or stepwise at normal temperature.

Specifically, for deodorizing hydrogen sulfide ($H_2S$), it is dehydrogenated, for example, to generate an HS group and an S group. The HS group is further oxidized to generate sulfuric acid ($H_2SO_4$), which is bonded to a metal. The S group is polymerized with a $CH_3S$ group obtained through dehydrogenation of methyl mercaptan as discussed below to generate methyl trisulfide ($CH_3$—S—S—S—$CH_3$) or methyl tetrasulfide ($CH_3$—S—S—S—S—$CH_3$), which is adsorbed to an adsorbent.

For deodorizing methyl mercaptan ($CH_3SH$) simultaneously with the deodorization of hydrogen sulfide ($H_2S$), it is dehydrogenated, for example, to generate a $CH_3S$ group. A portion of the $CH_3S$ group is oxidized to generate methanesulfonic acid ($CH_3SO_3H$), which is bonded to a metal. Another portion of the $CH_3S$ group is polymerized with the $CH_3S$ group itself to generate methyl disulfide ($CH_3$—S—S—$CH_3$), at least a portion of which is adsorbed to an adsorbent. Still another portion of the $CH_3S$ group is polymerized with the S group as discussed above to generate methyl trisulfide ($CH_3$—S—S—S—$CH_3$) or methyl tetrasulfide ($CH_3$—S—S—S—S—$CH_3$), which is physically adsorbed to an adsorbent.

A deodorizer according to the present invention includes a first metal oxide for removing malodor components at normal temperature by being bonded to the malodor components, a second metal oxide for assisting the first metal oxide in its deodorizing action, and an adsorbent for adsorbing the malodor components or products from the malodor components.

The first metal oxide should preferably comprise $MnO_2$ particles of an amorphous nature having a specific surface area of 200 $m^2/g$ or higher. The large specific surface area increases the reaction capability of the first metal oxide. It has been found that CuO is an excellent material for use as the second metal oxide.

Specifically, the deodorizer comprises $MnO_2$ (manganese oxide) particles which have a large specific surface area and are highly active, and CuO (copper oxide) particles which are carried on a surface of powdery or fibrous activated carbon.

Activated carbon such as coconut shell activated carbon or the like is excellent for use as a carrier for carrying the $MnO_2$ particles and also the CuO particles, because the large specific surface area increases the adsorbing capability.

In order to maintain the removal percentage of original odors at a high level, the $MnO_2$ particles and the CuO particles preferably are used in a weight ratio ranging from 8:2 to 4:6.

In order to satisfy the conditions of a high removal percentage of original odors and a low concentration of reaction products, the proportion of the total amount of $MnO_2$ particles and CuO particles to activated carbon is preferably in the range from 4:6 to 6:4 in terms of weight ratios.

A method of manufacturing a deodorizer according to the present invention comprises the steps of reacting a bivalent Mn compound and a septivalent Mn compound with each other, thereafter washing a reaction product with water and filtering the reaction product to produce amorphous $MnO_2$, dispersing the amorphous $MnO_2$ and activated carbon in an aqueous solution of a high concentration of copper salt, neutralizing the aqueous solution with an alkali, filtering and washing a resulting precipitate with water, and then drying the precipitate.

Preferably, the copper salt comprises $CuSO_4$ or $Cu(NO_3)_2$, and the alkali comprises NaOH or an aqueous solution of NaOH.

A deodorizing apparatus according to the present invention comprises a case having an air inlet and an air outlet, a fan housed in the case and rotatable by a motor for discharging air drawn from the air inlet out of the air outlet, and a deodorizer layer disposed on a surface of the fan, the deodorizer layer containing a deodorizer comprising $MnO_2$ (manganese oxide) particles which have a large specific surface area and are highly active, and CuO (copper oxide) particles which are carried on a surface of powdery or fibrous activated carbon. The deodorizing apparatus of the above structure may be incorporated in a toilet bowl.

BRIEF DESCRIPTION OF THE DRAWINGS

FIGS. 10(a)~10(c) are diagrams of XRD patterns showing how the number of water washing cycles affects the specific surface area of $MnO_2$, FIG. 10(a) showing an XRD pattern when the number of water washing cycles is 2, FIG. 10(b) showing an XRD pattern when the number of water washing cycles is 3, and FIG. 10(c) showing an XRD pattern when the number of water washing cycles is 4;

FIGS. 14(a)~14(c) are graphs showing comparative results of deodorizing effects achieved when the deodorizing apparatus according to the present invention and a conventional ozone deodorizing apparatus were incorporated in the seats with a warm water cleaning capability of toilet bowls (a seat with a built-in deodorizing fan and a seat with a built-in ozone deodorizing unit), FIG. 14(a) showing comparative results before the toilet bowls were used, FIG. 14(b) showing comparative results while the toilet bowls were being used, and FIG. 14(c) showing comparative results after the toilet bowls were used.

DETAILED DESCRIPTION OF BEST MODE FOR CARRYING OUT THE INVENTION

The present invention will hereinafter be described in detail with reference to the accompanying drawings.

In a deodorizing method according to the present invention, a polymerization reaction for polymerizing malodor components with each other, an oxidization reaction for oxidizing malodor components, and an adsorption reaction for adsorbing malodor components to an adsorbent are carried out simultaneously or stepwise at normal or room temperature.

Figure 1:
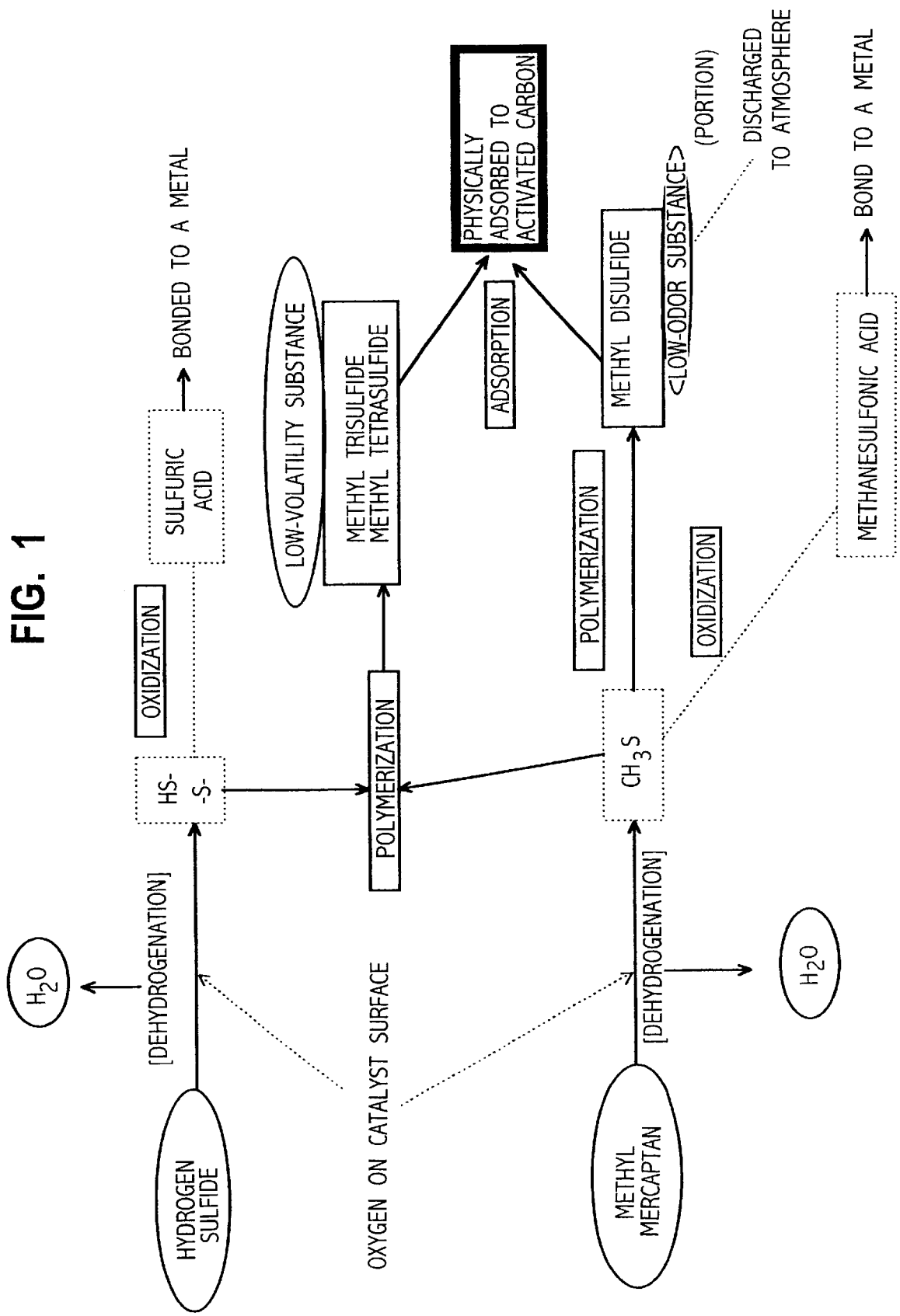
FIG. 1 is a diagram illustrative of a deodorizing method according to the present invention.

FIG. 1 schematically shows the deodorizing method according to the present invention. For deodorizing hydrogen sulfide ($H_2S$), it is dehydrogenated, for example, to generate an HS group and an S group. The HS group is oxidized to generate sulfuric acid ($H_2SO_4$), which is bonded to a metal. The S group is polymerized with a $CH_3S$ group to generate methyl trisulfide ($CH_3$—S—S—S—$CH_3$) or methyl tetrasulfide ($CH_3$—S—S—S—S—$CH_3$), which is adsorbed to an adsorbent.

For deodorizing methyl mercaptan ($CH_3SH$) simultaneously with the deodorization of hydrogen sulfide ($H_2S$), it is dehydrogenated, for example, to generate a $CH_3S$ group. A portion of the $CH_3S$ group is oxidized to generate methanesulfonic acid ($CH_3SO_3H$), which is bonded to a metal. Another portion of the $CH_3S$ group is polymerized with the $CH_3S$ group itself to generate methyl disulfide ($CH_3$—S—S—$CH_3$), at least a portion of which is adsorbed to an adsorbent. Still another portion of the $CH_3S$ group is polymerized with the S group from the dehydrogenated $H_2S$ to generate methyl trisulfide ($CH_3$—S—S—S—$CH_3$) or methyl tetrasulfide ($CH_3$—S—S—S—S—$CH_3$), which is physically adsorbed to an adsorbent.

A deodorizer according to the present invention includes a first metal oxide for removing malodor components at normal temperature by being bonded to the malodor components, a second metal oxide for assisting the first metal oxide in its action, and an adsorbent for adsorbing the malodor components or products from the malodor components.

The first metal oxide should preferably comprise $MnO_2$ particles of an amorphous nature having a specific surface area of 200 $m^2/g$ or higher. The large specific surface area increases the reaction capability of the first metal oxide.

Figure 2:
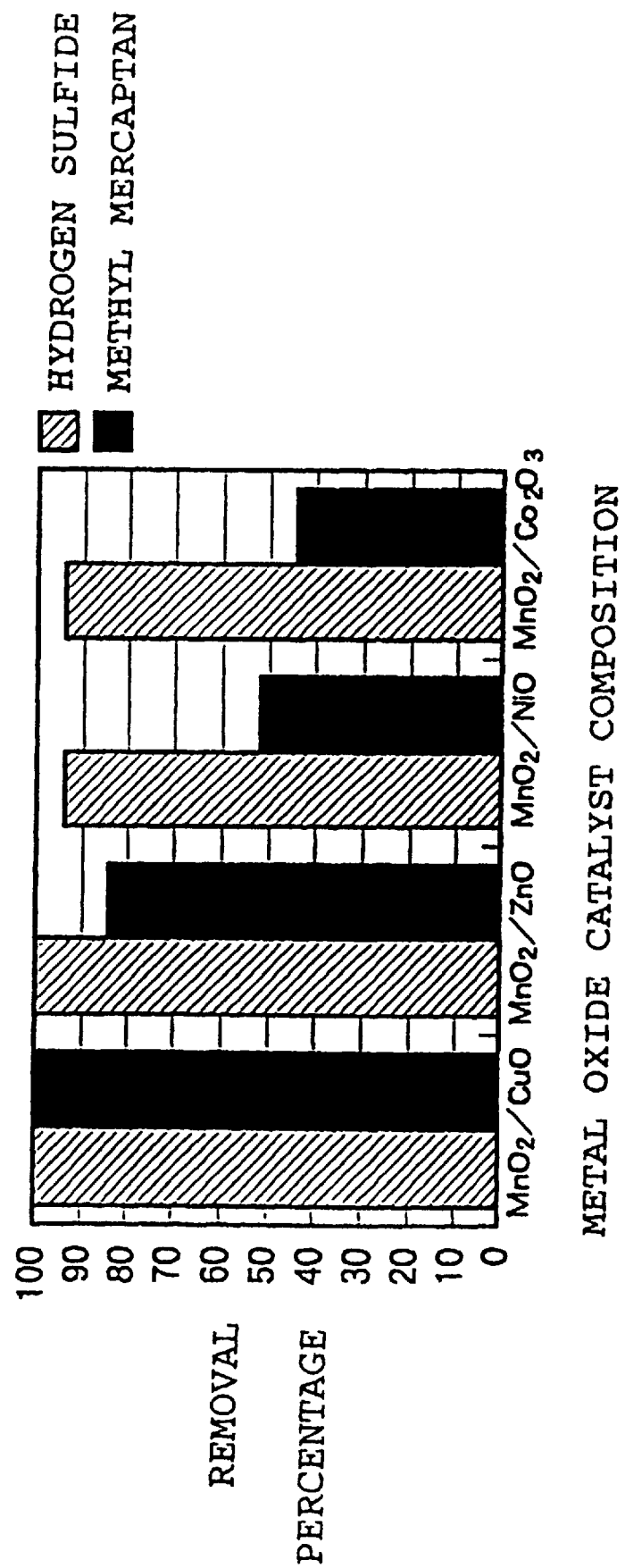
FIG. 2 is a graph showing removal percentages of original odors (hydrogen sulfide and methyl mercaptan) processed using mixtures of $MnO_2$ particles and various second metal oxide particles.

FIG. 2 is a graph showing removal percentages of original odors (hydrogen sulfide and methyl mercaptan) processed using mixtures of $MnO_2$ particles and various second metal oxide particles ($MnO_2$/CuO, $MnO_2$/ZnO, $MnO_2$/NiO, $MnO_2$/$CO_2O_3$). It can be seen from the graph that CuO is excellent for use as the second metal oxide.

Figure 3:
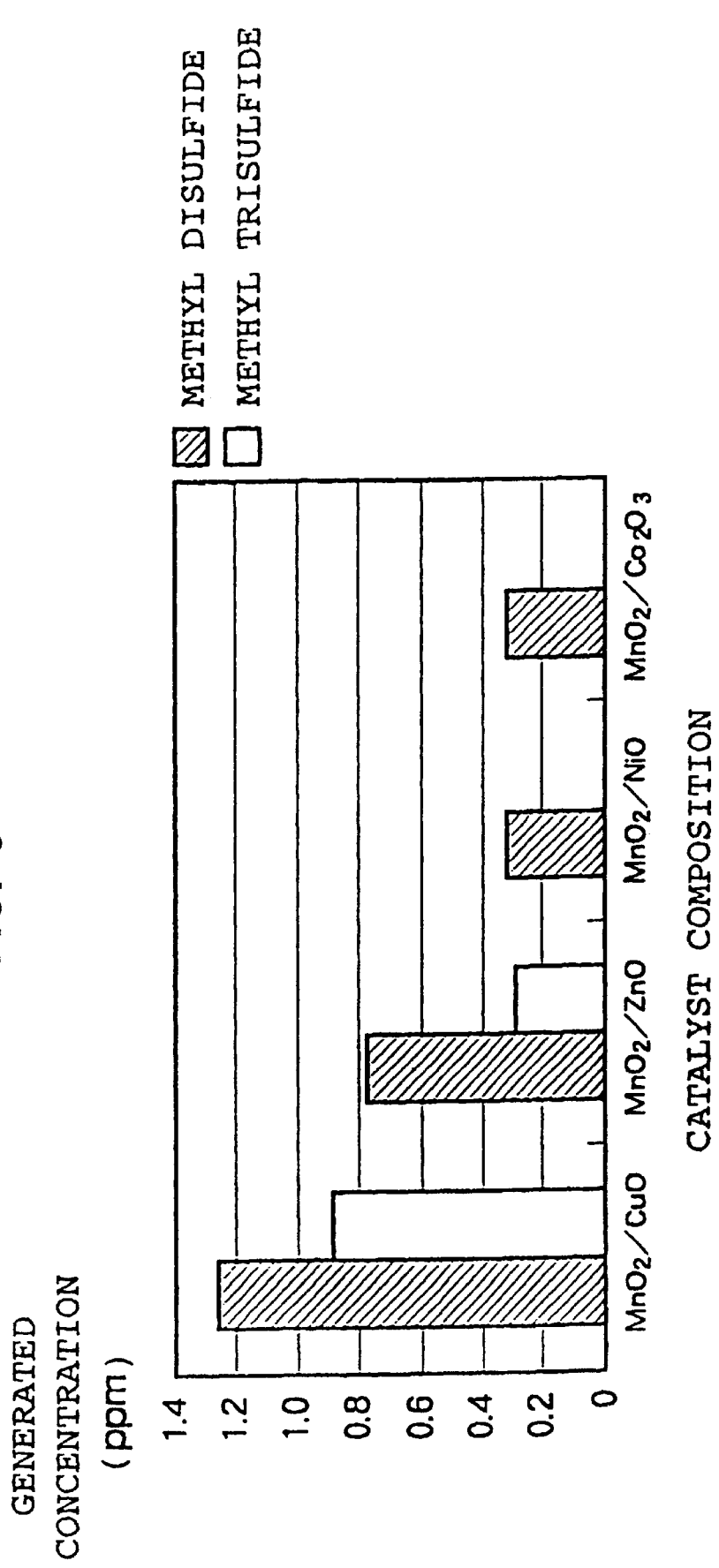
FIG. 3 is a graph showing the results of an analysis of reaction products discharged as outlet gases from a deodorizing apparatus using mixtures of $MnO_2$ particles and various second metal oxide particles.

FIG. 3 is a graph showing the results of an analysis of reaction products discharged as outlet gases from a deodorizing apparatus using mixtures of $MnO_2$ particles and various second metal oxide particles. A study of FIG. 3 indicates that methyl disulfide ($CH_3$—S—S—$CH_3$), etc. is generated by a polymerization of methyl mercaptan with any of the compositions.

Figure 4:
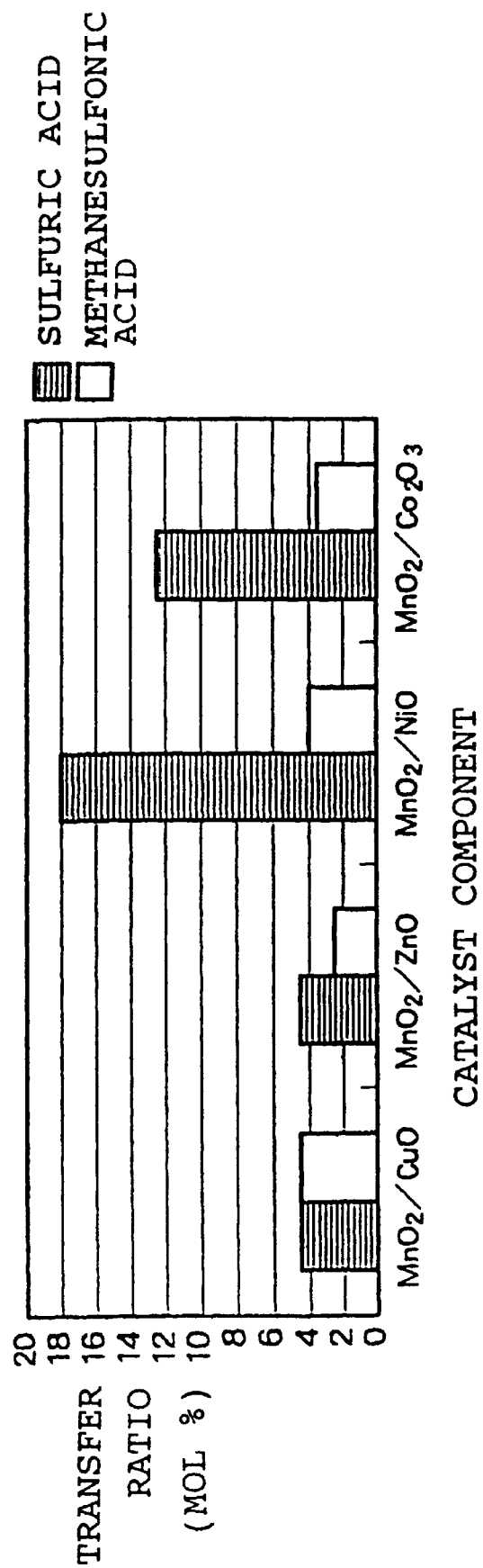
FIG. 4 is a graph showing the results of an analysis of substances remaining on the surface of a deodorizer after malodors were removed using mixtures of $MnO_2$ particles and various second metal oxide particles.

FIG. 4 is a graph showing the results of an analysis of substances remaining on the surface of a deodorizer after malodors were removed using mixtures of $MnO_2$ particles and various second metal oxide particles. A study of FIG. 4 reveals that methanesulfonic acid ($CH_3SO_3H$) is generated with any of the compositions.

It can be understood from the above analyses of the reaction products that a polymerization reaction and an oxidization reaction occur with any of the metal oxide compositions though the reacting weights involved in these reactions vary from each other. Another analysis has confirmed that a harmful gas of SOx is not generated.

With the composition of a mixture of $MnO_2$ particles and CuO particles which exhibits high malodor removal percentages, methyl disulfide and methyl trisulfide which is problematic as a malodor component are generated in large quantities, and it is necessary to adsorb these substances so as not to discharge them out.

Figure 5:
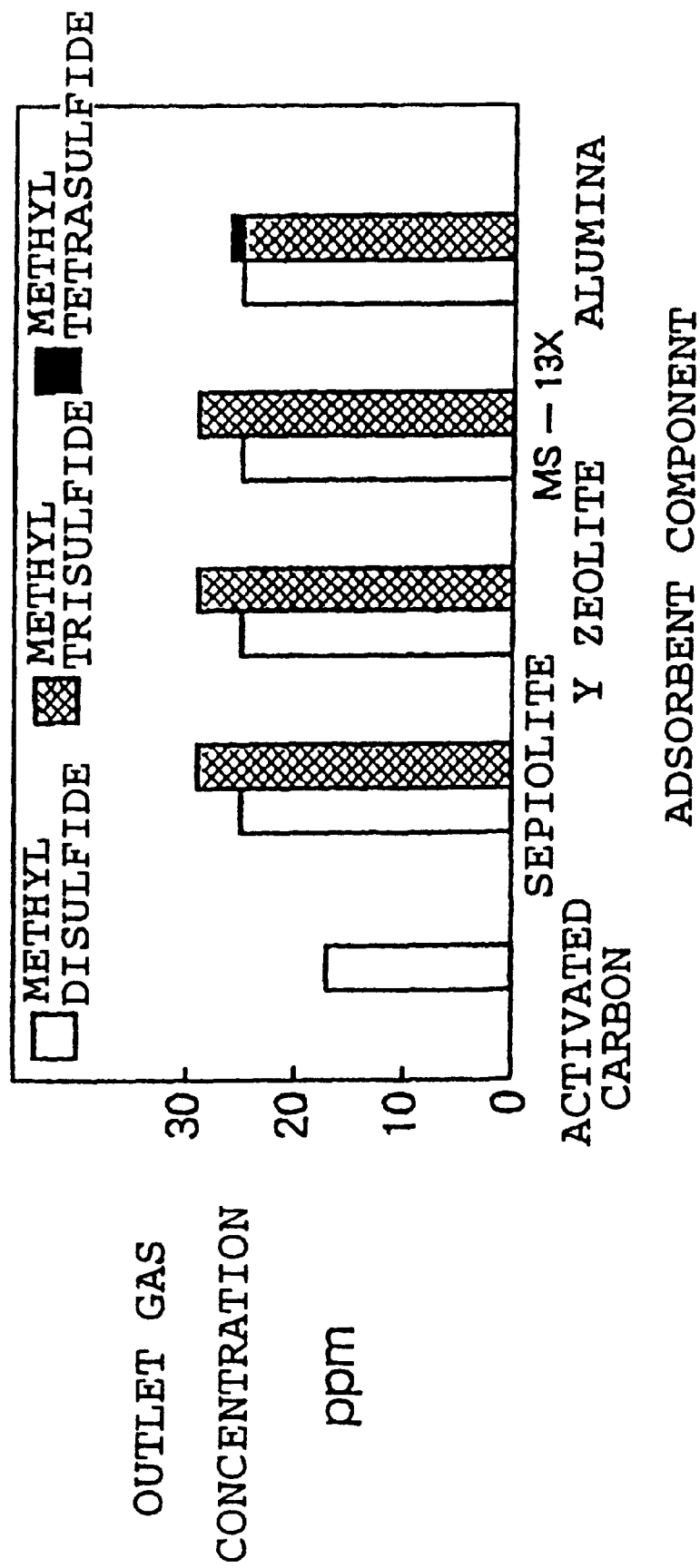
FIG. 5 is a graph showing the results of an analysis of reaction products discharged as outlet gases from a deodorizing apparatus using $MnO_2$ particles and CuO particles carried by various carriers.

FIG. 5 is a graph showing the results of an analysis of reaction products discharged as outlet gases from a deodorizing apparatus using $MnO_2$ particles and CuO particles mixed with various adsorbents. It can be seen from FIG. 5 that activated carbon is an excellent material for adsorbing malodor components to prevent them from being discharged. In particular, activated carbon such as coconut shell activated carbon or the like is excellent for use as a carrier for carrying $MnO_2$ (manganese oxide) particles which have a large specific surface area and are highly active, and also CuO (copper oxide) particles, because the large specific surface area increases the adsorbing capability of the activated carbon. As described above, it is preferable that the $MnO_2$ particles have a specific surface area of 200 $m^2/g$ or higher and be substantially amorphous.

Figure 6:
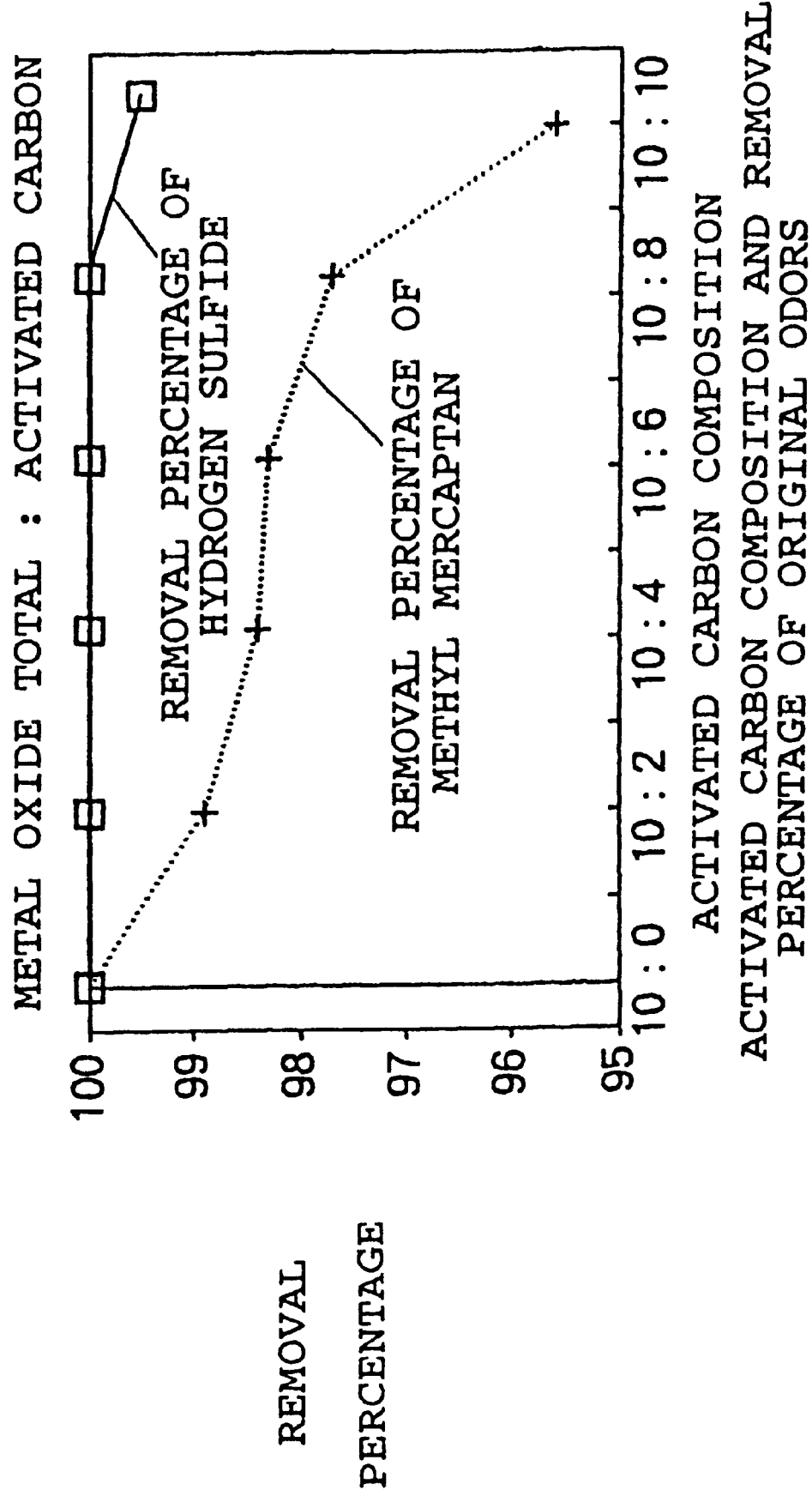
FIG. 6 is a graph showing the relationship between the composition ratio of activated carbon and the removal percentages of original odors (hydrogen sulfide and methyl mercaptan)
Figure 7:
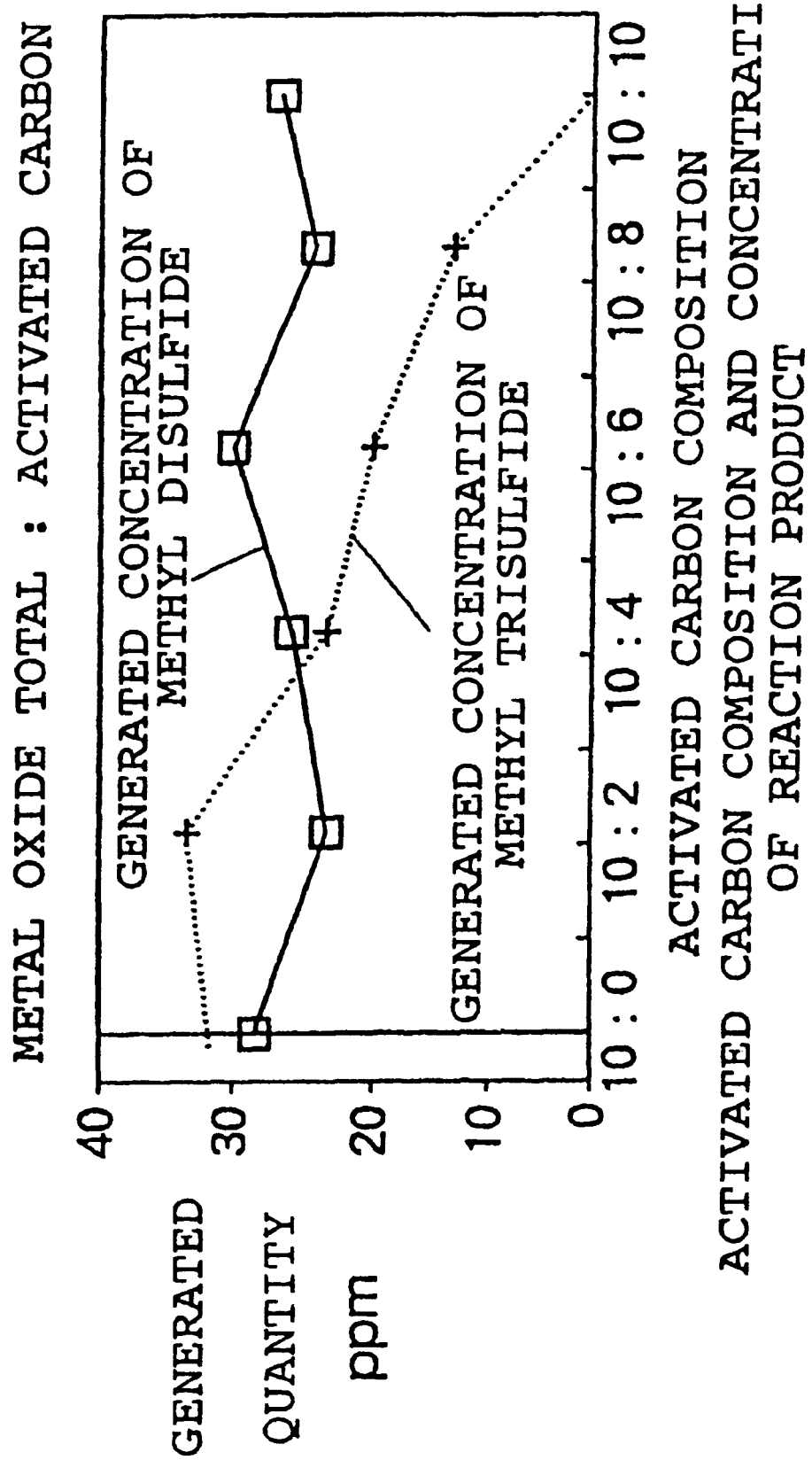
FIG. 7 is a graph showing the relationship between the composition ratio of activated carbon and the concentrations of reaction products (methyl disulfide and methyl trisulfide)

FIG. 6 is a graph showing the relationship between the composition ratio of activated carbon and the removal percentages of original odors (hydrogen sulfide and methyl mercaptan), and FIG. 7 is a graph showing the relationship between the composition ratio of activated carbon and the concentrations of reaction products (methyl disulfide and methyl trisulfide). In order to satisfy the conditions of high removal percentages of original odors and low concentrations of reaction products, it is suitable for the proportion of the total amount of $MnO_2$ particles and CuO particles to activated carbon to be in the range from 4:6 to 6:4 in terms of weight ratios.

Figure 8:
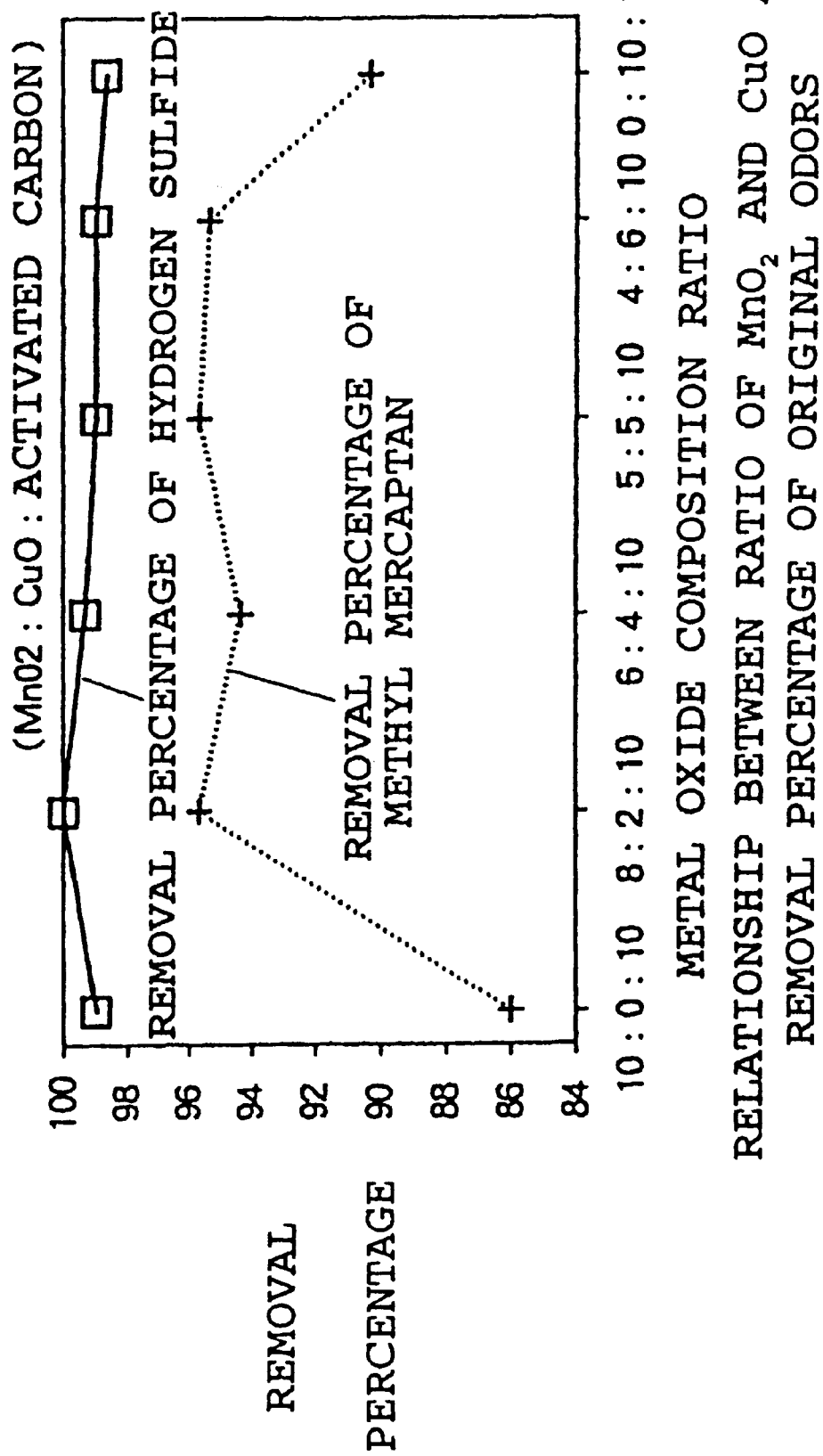
FIG. 8 is a graph showing the relationship between the composition ratios of $MnO_2$ and CuO and the removal percentages of original odors.

FIG. 8 is a graph showing the relationship between the composition ratios of $MnO_2$ and CuO for a given proportion of total metal oxide particles to activated carbon of 1:1, and the removal percentages of original odors. It can be understood from the graph that the weight ratios of $MnO_2$ and CuO should preferably in the range from 8:2 to 4:6 in order to maintain high removal percentages of original odors.

In a method of manufacturing a deodorizer according to the present invention, after a bivalent Mn compound and a septivalent Mn compound are reacted with each other, the reaction product is washed with water and filtered to produce amorphous $MnO_2$, the amorphous $MnO_2$ and activated carbon are dispersed in an aqueous solution of a high concentration of copper salt, then the aqueous solution is neutralized by an alkali, and a precipitate is filtered and washed with water and then dried. In the state of such precipitate the $MnO_2$ and CuO particles are intimately combined with the activated carbon and carried on surfaces of the carbon.

In the above method of manufacturing a deodorizer, the copper salt should preferably be $CuSO_4$ or $Cu(NO_3)_2$, and the alkali should preferably be NaOH or an aqueous solution of NaOH.

A deodorizing apparatus according to the present invention has a layer of the deodorizer described above on a surface of a fan for drawing air from an air inlet and delivering the air to an air outlet. Because the deodorizing apparatus is of a simple structure, it can be incorporated in a toilet bowl.

Figure 9:
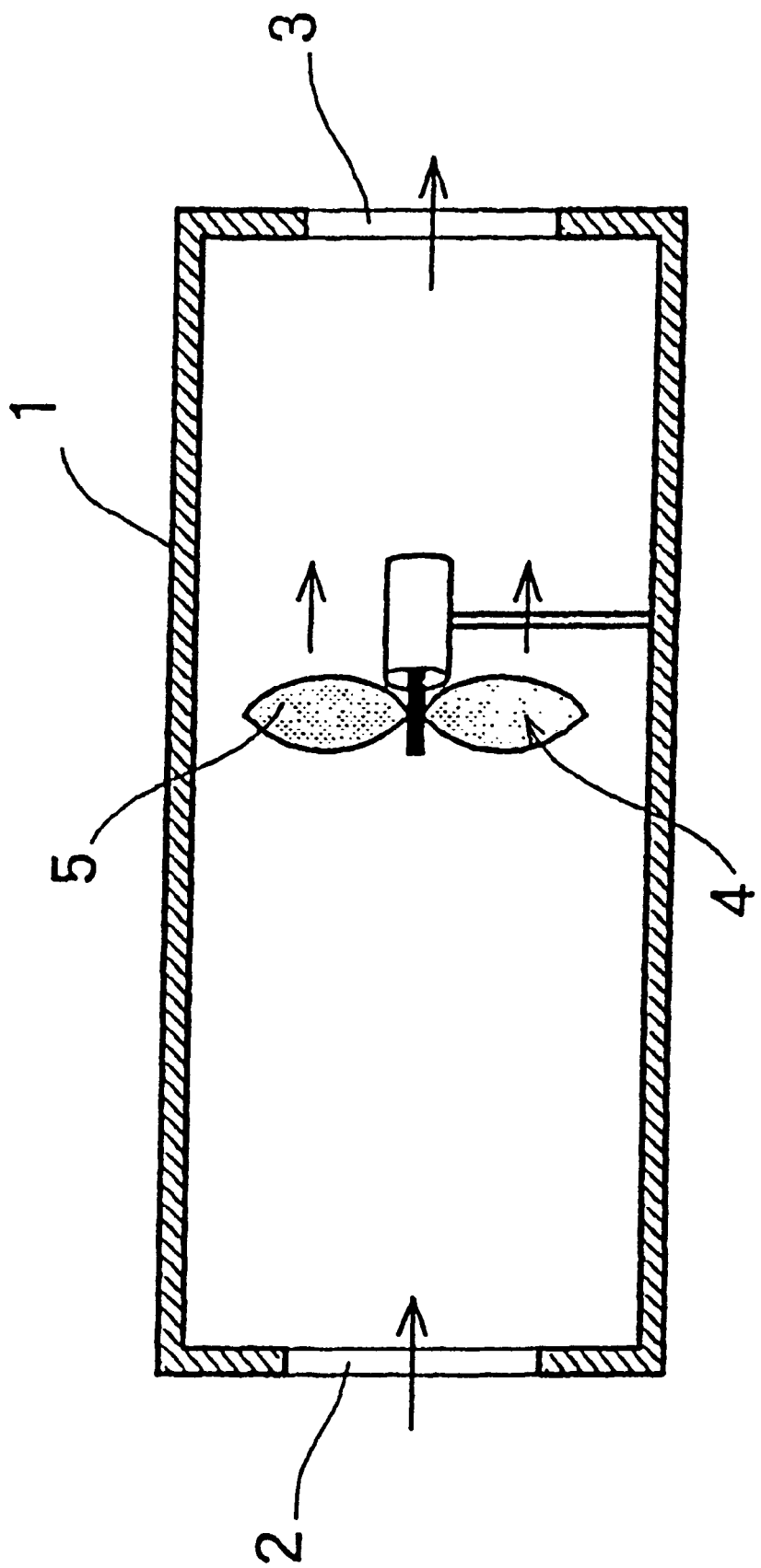
FIG. 9 is a schematic view of a deodorizing apparatus which incorporates a deodorizer according to the present invention.

FIG. 9 shows a specific arrangement of the deodorizing apparatus which incorporates the deodorizer according to the present invention. The deodorizing apparatus comprises a case 1 having an air inlet 2 and an air outlet 3, a fan 4 housed in the case 1 and rotatable by a motor, and a deodorizer layer 5 disposed on a surface of the fan 4, the deodorizer layer 5 comprising the deodorizer according to the above embodiment.

The deodorizer layer 5 is formed by coating and drying a slurry which is produced by kneading the deodorizer with an organic binder. The deodorizer comprises $MnO_2$ particles which have a large specific surface area and are highly active, and CuO (copper oxide) particles which are carried on the surface of activated carbon in the form of a powder or fibers.

Specifically, the method of manufacturing the deodorizer comprises the first step of preparing substantially amorphous $MnO_2$ particles and the second step of carrying the $MnO_2$ particles and the Cu particles on activated carbon.

In the first step of preparing $MnO_2$ particles, a bivalent Mn compound and a septivalent Mn compound are reacted with each other, and thereafter the reaction product is washed with water and filtered to produce amorphous $MnO_2$. More specifically, for example a hydrate of manganese sulfate in an amount corresponding to 0.4 mol of Mn is introduced into 56.8 g of water, and 272 g of 95% sulfuric acid is then gradually introduced into the liquid while stirring the same. Since the liquid generates heat, it is cooled and kept at a temperature ranging from 70 to 75° C. Then, 60 g of potassium permanganate is gradually introduced into the liquid, which is cooled and kept at a temperature ranging from 60 to 65° C. as it generates heat.

The liquid thus obtained, which is of a thick purple color and is highly viscous, is introduced into 10 liters of water. After the solution is washed with water and filtered in four repeated cycles, it is dried at 110° C., producing about 65 g of $MnO_2$ which is of a thick brown color.

Figure 10A:
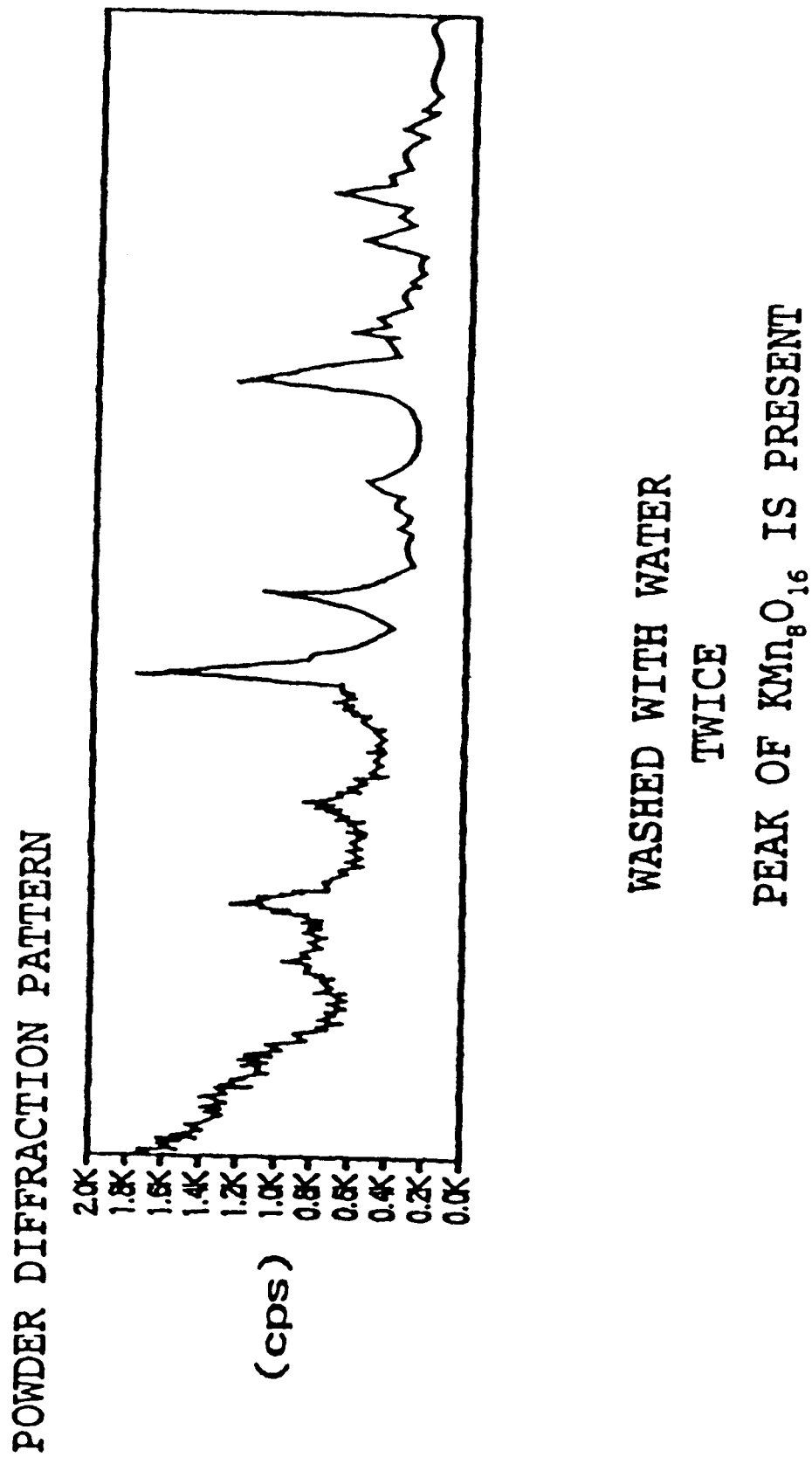
Figure 10B:
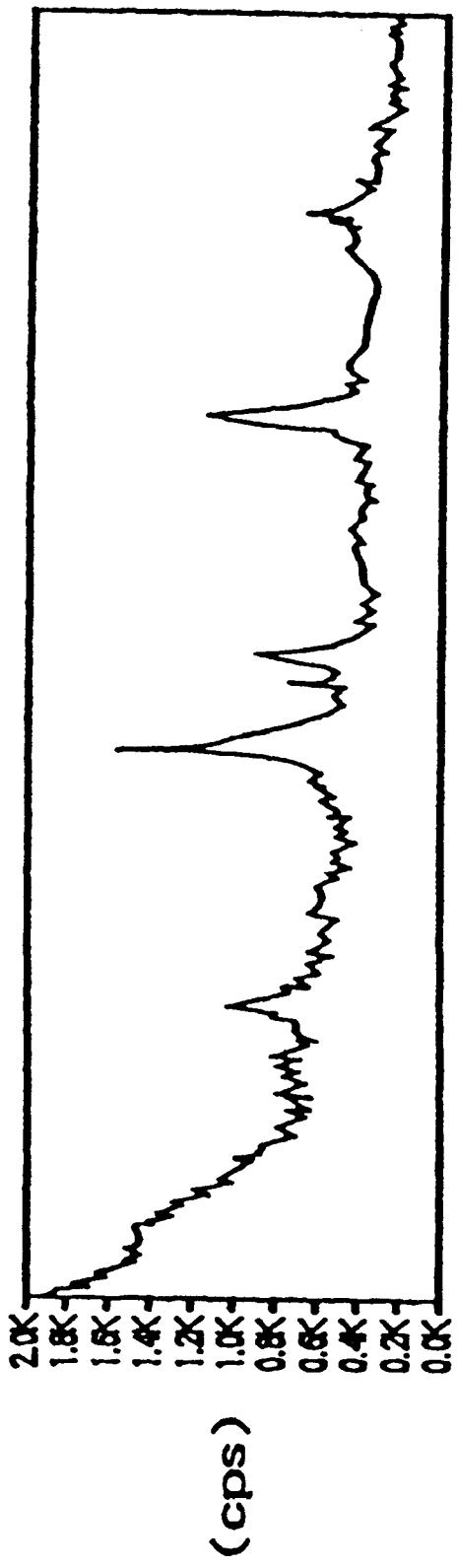

X-ray diffraction patterns of the $MnO_2$ thus obtained are shown in FIGS. 10(a)–10(c). The $MnO_2$ was analyzed by X-ray diffraction with a radiation source of Cu, a tube voltage of 50 KV, a tube current of 300 mA, and a monochromatic meter.

FIG. 10(a) shows an X-ray diffraction pattern produced when the solution is washed with water and filtered in two repeated cycles. As can be seen from FIG. 10(a), when the solution is washed with water and filtered in only two repeated cycles, a peak of $KMn_8O_{16}$ is recognized, and the specific surface area is of a small value of 94 $m^2/g$. FIG. 10(b) shows an X-ray diffraction pattern produced when the solution is washed with water and filtered in three repeated cycles. When the solution is washed with water and filtered in three repeated cycles, the specific surface area increases to a larger value of 131 $m^2/g$, but the $MnO_2$ remains crystalline. FIG. 10(c) shows an X-ray diffraction pattern produced when the solution is washed with water and filtered in four repeated cycles. When the solution is washed with water and filtered in four repeated cycles, as shown in FIG. 10(c), the specific surface area increases to a much larger value of 235 $m^2/g$, and the $MnO_2$ becomes amorphous.

Figure 11:
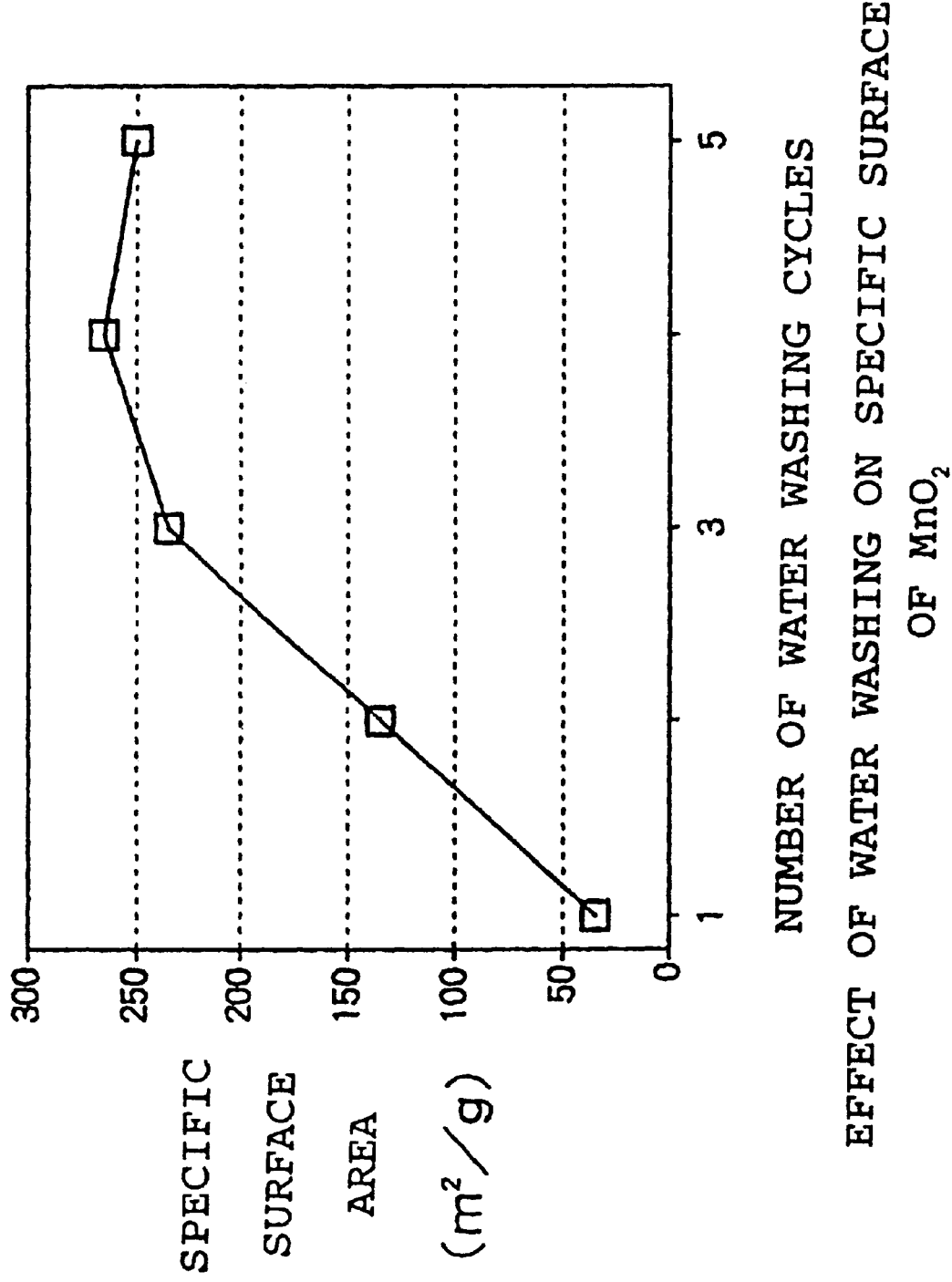
FIG. 11 is a graph showing the relationship between the specific surface area of $MnO_2$ and the number of water washing cycles.

FIG. 11 is a graph showing the relationship between the specific surface area of MnO$_2$ and the number of water washing cycles. Since the adsorbing capability increases as the specific surface area increases, the number of water washing cycles should preferably be four or more.

In the second step, the MnO$_2$ particles of substantially amorphous nature having a specific surface area of 200 m$^2$/g or higher, which have been produced in the first step, are mixed with CuO and activated carbon, and the MnO$_2$ particles and the CuO particles are carried on the activated carbon by a precipitation carrying process.

Figure 12:
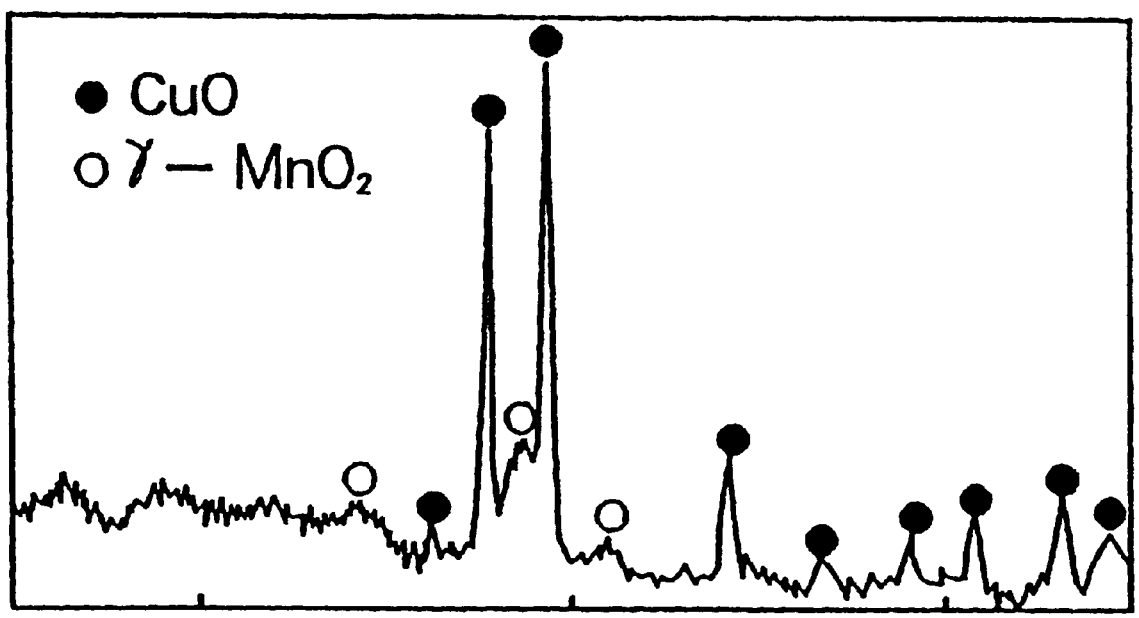
FIG. 12 is a diagram showing an XRD pattern of the deodorizer.

Specifically, for example 315 g of a pentahydrate of copper sulfate is dissolved into 1250 g of water, and then 150 g of a powder produced by grinding the MgO$_2$ described above with a mortar and 250 g of powdery activated carbon are dispersed in the solution, which is then stirred uniformly. Then, 3750 g of 1 N of caustic soda is introduced into the solution, which is thereafter stirred for 18 hours. Then, 5 liters of water is added to the mixture, which is filtered and washed with water in three repeated cycles, and then dried. The dried mass is crushed into about 500 g of a deodorizer in which fine MgO$_2$ and CuO crystal are dispersed and carried on the surface of activated carbon. It can be seen from FIG. 12 that fine MgO$_2$ and CuO crystal are dispersed and carried on the surface of activated carbon.

The activated carbon should preferably be coconut shell activated carbon having a specific surface area of 500 m$^2$/g or higher. The activated carbon may be in the form of a powder or fibers.

Figure 13:
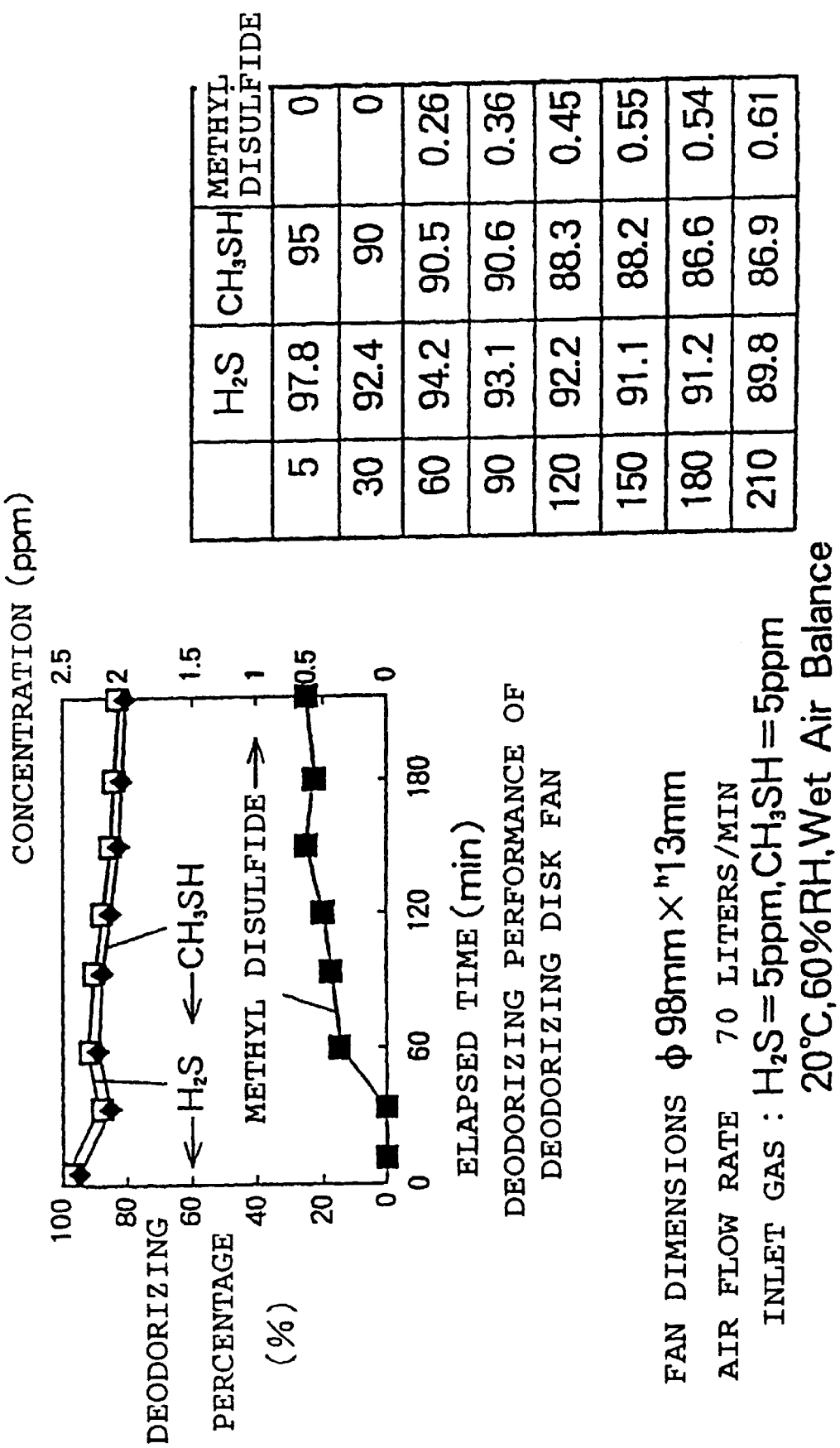
FIG. 13 is a graph showing experimental results of deodorizing effects of the deodorizing apparatus.

In order to confirm deodorizing effects of the deodorizing apparatus which incorporates the deodorizer according to the present invention, the apparatus shown in FIG. 9 was fabricated and experimented. The results of the experiment are shown in FIG. 13. The experiment was conducted with fan dimensions of 98 mm (diameter)×13 mm (height), an air flow rate of 70 liters/min., 5 ppm of H$_2$S at the air inlet, 5 ppm of CH$_3$SH at the air inlet, a temperature of 20° C., and a humidity of 60%.

It will be understood from FIG. 13 that when the deodorizing apparatus according to the present invention is used, the removal percentage of the original odors can be kept at 90% or higher for a long period of time, methyl disulfide (CH$_3$—S—S—CH$_3$) is generated in a small percentage of about 10%, and hence methyl trisulfide (CH$_3$—S—S—S—CH$_3$) is generated in a concentration of 0.1 ppm or less.

For human beings to clearly recognize that malodors have been removed, it is necessary that the odor intensity be reduced one step or more. Since the odor intensity is exponentially related to the odor concentration, reducing the odor intensity one step or more is equivalent to reducing the concentration of the original odors to $\frac{1}{10}$ or less. This means that the removal percentage of the original odors should be 90% or more.

Deodorizing effects obtained when the above deodorizing apparatus was incorporated in the seats with a warm water cleaning capability of toilet bowls were evaluated. The results of the evaluation are shown in FIGS. 14(a) through 14(c).

FIGS. 14(a) through 14(c) are graphs showing comparative results of questionnaires on deodorizing effects achieved when the deodorizing apparatus according to the present invention and a conventional ozone deodorizing apparatus were incorporated in the seats with a warm water cleaning capability of toilet bowls, i.e., a seat with a built-in deodorizing fan and a seat with a built-in ozone deodorizing unit. FIG. 14(a) shows comparative results before the toilet bowls were used. FIG. 14(b) shows comparative results while the toilet bowls were being used. FIG. 14(c) shows comparative results after the toilet bowls were used.

As shown in FIGS. 14(a) through 14(c), it has been confirmed that the deodorizing apparatus according to the present invention achieved substantially the same deodorizing effects as the conventional deodorizing apparatus.

According to the present invention, as described above, a polymerization reaction, an oxidization reaction, and an adsorption reaction are carried out simultaneously or stepwise at normal temperature for removing malodor components and preventing harmful products from being discharged.

Particularly, MnO$_2$ which has a strong oxidizing ability at normal temperature and CuO which assists the MnO$_2$ in its oxidizing action are combined with each other to allow the polymerization reaction and the oxidization reaction to be carried out efficiently, and powdery or fibrous activated carbon is used to effectively prevent harmful or malodorous products from being discharged.

MnO$_2$ particles which have a specific surface area of 200 m$^2$/g or higher and are substantially amorphous are selected, the weight ratios of MnO$_2$ particles and CuO particles are in the range from 8:2 to 4:6, and the proportion of the total amount of MnO$_2$ particles and CuO particles to activated carbon is in the range from 4:6 to 6:4 in terms of weight ratios. With these values, it is possible to effectively suppress the generation and discharge of methyl trisulfide.

According to the method of manufacturing a deodorizer, after a bivalent Mn compound and a septivalent Mn compound are reacted with each other, the reaction product is washed with water and filtered to produce amorphous MnO$_2$, and the amorphous MnO$_2$ and activated carbon are dispersed in an aqueous solution of a high concentration of copper salt such as CuSO$_4$ or Cu(NO$_3$)$_2$. In this manner, a deodorizer according to the present invention is manufactured.

Since a layer of the above deodorizer is formed on a fan of a deodorizing apparatus, the deodorizing apparatus is compact and requires no periodic replacement. When the deodorizing apparatus is incorporated in a toilet bowl, for example, the toilet bowl is given an increased value.

Although there have been disclosed what are at present considered to be the preferred embodiments of the invention, it will be understood by persons skilled in the art that variations and modifications may be made thereto without departing from the spirit or essence of the invention. The scope of the invention is indicated by the appended claims, rather than by the foregoing description.

We claim:

1. A deodorizer comprising a first metal oxide for removing malodor components at normal temperature by being bonded to the malodor components, a second metal oxide for assisting the first metal oxide in a deodorizing action thereof, and an adsorbent for adsorbing products from the malodor components;

said first and second metal oxides being in the form of fine particles, said adsorbent comprising at least one of powdery and fibrous activated carbon, and said first and second metal oxide particles being intimately combined with the adsorbent and carried on surfaces of the adsorbent.

2. A deodorizer according to claim 1, wherein said first metal oxide comprises MnO$_2$ particles having a specific surface area of at least 200 m$^2$/g.

3. A deodorizer according to claim 1, wherein said first metal oxide comprises MnO$_2$ particles having a substantially amorphous structure.

4. A deodorizer according to claim 1, wherein said second metal oxide comprises CuO particles.

5. A deodorizer according to claim 1, wherein said first metal oxide comprises $MnO_2$ particles and said second metal oxide comprises CuO particles, a weight ratio of said $MnO_2$ particles to said CuO particles ranging from 8:2 to 4:6.

6. A deodorizer according to claim 1, wherein said first metal oxide comprises $MnO_2$ particles, said second metal oxide comprises CuO particles, said adsorbent comprises activated carbon, and wherein the proportion of a total amount of $MnO_2$ particles and CuO particles to activated carbon is in the range from 4:6 to 6:4 in terms of weight ratios.

7. A deodorizer according to claim 1, further including an organic binder combined with the first and second metal oxides and the adsorbent such that the deodorizer may be applied as a thin layer to a surface of an object.

8. A deodorizer according to claim 1, wherein said first metal oxide particles are adapted to catalyze a polymerization and an oxidation of the malodor components as the deodorizing action thereof, and said adsorbent is adapted to adsorb at least products from the polymerization of the malodor components.

9. A deodorizer according to claim 1, wherein said adsorbent comprises activated carbon having a specific surface area of at least 500 $m^2/g$.

10. A deodorizer according to claim 1, wherein said activated carbon is made from coconut shell.

11. A deodorizing apparatus comprising a case having an air inlet and an air outlet, a fan housed in said case and rotatable by a motor for discharging air drawn from said air inlet out of said air outlet, and a deodorizer layer disposed on a surface of said fan, said deodorizer layer comprising a first metal oxide for removing malodor components from the air at normal temperature by being bonded to the malodor components, a second metal oxide for assisting the first metal oxide in a deodorizing action thereof, and an adsorbent for adsorbing products from the malodor components; said first and second metal oxides being in the form of fine particles, said said first metal oxide comprises $MnO_2$ particles having a substantially amorphous structure, and said first and second metal oxide particles being carried on surfaces of the adsorbent.

12. A deodorizing apparatus according to claim 11, wherein said case is incorporated in a toilet bowl.

13. A deodorizing apparatus according to claim 11, wherein said first metal oxide comprises active $MnO_2$ which have a specific surface area $\geq 200$ $m^2/g$, and said second metal oxide comprises CuO particles which are carried on a surface of the adsorbent, and the adsorbent comprises powdery or fibrous activated carbon.

14. A deodorizing apparatus according to claim 11, wherein said first metal oxide particles are adapted to catalyze a polymerization and an oxidation of the malodor components as the deodorizing action thereof, and said adsorbent is adapted to adsorb at least products from the polymerization and the oxidation of the malodor components.

15. A deodorizing apparatus according to claim 11, wherein said adsorbent comprises activated carbon having a specific surface area of at least 500 $m^2/g$.

16. A method of manufacturing a deodorizer, comprising the steps of reacting a bivalent Mn compound and a septivalent compound with each other, thereafter washing a reaction product with water and filtering the reaction product to produce amorphous $MnO_2$, dispersing the amorphous $MnO_2$ and at least one of powdery and fibrous activated carbon in an aqueous solution having a high concentration of copper salt, neutralizing the aqueous solution with an alkali, filtering and washing a precipitate of the dispersion with water, and then drying the precipitate.

17. A method according to claim 16, wherein said copper salt comprises at least one of $CuSO_4$ and $Cu(NO_3)_2$.

18. A method according to claim 16, wherein said alkali comprises NaOH.

* * * * *

UNITED STATES PATENT AND TRADEMARK OFFICE
CERTIFICATE OF CORRECTION

PATENT NO. : 6,010,666
DATED : January 4, 2000
INVENTOR(S) : T. Kurokawa, et. al.

It is certified that error appears in the above-identified patent and that said Letters Patent is hereby corrected as shown below:

On the cover page, in the "[57] ABSTRACT", 1st line, change "a HS group" to ——an HS group——.

Column 4, line 59, change "$CO_2O_3$" to ——$Co_2O_3$——.

Column 5, line 50, after "preferably" insert ——be——.

Column 6, line numbered between 30 and 31, after "example" insert a comma.

Column 7, line 12, after "example" insert a comma.

Column 10, line 2 (claim 11, line 12), change "said said" to ——said——;
line 9 (claim 13, line 2) after "$MnO_2$" insert ——particles——;
line 26 (claim 16, line 3), before "compound" insert ——Mn——.

Signed and Sealed this

Twelfth Day of September, 2000

Attest:

Q. TODD DICKINSON

*Attesting Officer*  *Director of Patents and Trademarks*